United States Patent
Prior et al.

(10) Patent No.: US 9,235,684 B2
(45) Date of Patent: Jan. 12, 2016

(54) MODELING LONG-TERM HOST-PATHOGEN INTERACTIONS

(75) Inventors: Steven David Prior, Reston, VA (US); Kenneth A. De Jong, Annandale, VA (US); Jayshree Sarma, Herndon, VA (US)

(73) Assignee: George Mason Intellectual Properties, Inc., Fairfax, VA (US)

(*) Notice: Subject to any disclaimer, the term of this patent is extended or adjusted under 35 U.S.C. 154(b) by 1430 days.

(21) Appl. No.: 10/900,352

(22) Filed: Jul. 28, 2004

(65) Prior Publication Data

US 2005/0055188 A1    Mar. 10, 2005

Related U.S. Application Data

(60) Provisional application No. 60/490,430, filed on Jul. 28, 2003.

(51) Int. Cl.
*G06F 19/00* (2011.01)

(52) U.S. Cl.
CPC ........ *G06F 19/3437* (2013.01); *G06F 19/3493* (2013.01)

(58) Field of Classification Search
None
See application file for complete search history.

(56) References Cited

PUBLICATIONS

An G. Shock, vol. 16, pp. 266-273, 2001.*
Dixon et al. Cellular Microbiology, vol. 2, pp. 453-463, 2000.*
Gonzalez et al. Biosystems, vol. 68, pp. 171-185, Feb.-Mar. 2003.*
Bagni et al. (Journal of Artificial Societies and Social Simulation vol. 5, No. 3, Jun. 20, 2002, web version web.archive.org/web/20020805201132/http://jasss.soc.surrey.ac.uk/5/3/5.html [Accessed online on Oct. 11, 2007]).*
Yahja (BioWar Simulation and Causality in CASOS Conference Day 1, p. 55-68, Jun. 21, 2002).*
Minar et al. (The Swarm simulation system: A toolkit for building multi-agent simulations. Working Paper 96-06-042, Santa Fe Institute, Santa Fe. 1996).*
Langton et al. (http://www.santafe.edu/projects/swarm, Apr. 1995 [accessed from (http://netresearch.ics.uci.edu/Previous_research_projects/agentos/related/swarm/swarmdoc.pdf)]).*
Epstein et al. (Center on Social and Economic Dynamics, Working Paper No. 31, Dec. 2002, accessed online [http://citeseerx.ist.psu.edu/viewdoc/summary?doi=10.1.1.134.8829]).*

* cited by examiner

*Primary Examiner* — Lori A. Clow
(74) *Attorney, Agent, or Firm* — Eckert Seamans Cherin & Mellott, LLC

(57) ABSTRACT

Using an in silico testing environment, host-pathogen interactions can be modeled and simulated by, in any effective order, identifying a plurality of biological events associated with a pathogen's invasion of a host; identifying for each biological event, at least one agent associated with the event; describing the state for each agent and/or identifying at least one action for each agent; identifying at least one interaction between agents; simulating a temporal course of the host-pathogen interaction using the plurality of biological events; and displaying the results of the simulation phase. The simulation phase may be accomplished using an agent-based simulation system that includes a feedback loop. The feedback loop is configured for continuously using output of at least one simulation as input for at least another simulation until an end is met.

19 Claims, 11 Drawing Sheets

FIG. 6

```
                   ┌──────────────┐     ┌─────┐           ┌─────┐
┌─────────┐        │ Anthrax Spore│◄────┤ No  │◄─────────►│ Yes │
│ Agent 1 │        └──────┬───────┘     └─────┘           └─────┘
└─────────┘               │                ▲                 │
                          ▼                │                 │
┌─────────┐       ┌──────────────┐   ┌─────────────┐         │
│ Agent 2 │       │ Contact with │   │Spore Clearance?        │
└─────────┘       │  Alveolar    │   └─────────────┘         │
                  │ Macrophage?  │         ▲                 │
                  └──────┬───────┘         │                 │
                    Yes ◄┴► No                               │
                     │      │                                │
                     ▼      └─────────────────┐              │
              ┌────────────┐                   │             │
              │Phagocytosis│    ┌─────────┐    │             ▼
              └─────┬──────┘    │ Agent 3 │    │      ┌──────────────┐
                    ▼           └─────────┘    │      │Infection     │
              ┌────────────┐                   │      │Resolved      │
              │Germination │                   │      └──────────────┘
              └─────┬──────┘                   │             ▲  ▲
                Yes ◄┴► No ──────────────────────────────────┘  │
                 │                                              │
                 ▼           ┌─────────┐                        │
         ┌──────────────┐    │ Agent 4 │                        │
         │Release from  │    └─────────┘                        │
         │Phagosome?    │                                       │
         └──────┬───────┘                                       │
           Yes ◄┴► No ────────────────────────────────────────┘
            │
            ▼
   ┌──────────────────┐   ┌─────────┐
   │Vegetative Anthrax│   │ Agent 5 │
   │Cells in Cytoplasm│   └─────────┘
   └──────────────────┘
```

FIG. 11

MODELING LONG-TERM HOST-PATHOGEN INTERACTIONS

CROSS-REFERENCE TO RELATED APPLICATIONS

The present application claims the benefit of provisional patent application: Ser. No. 60/490,430 to Prior et al., filed on Jul. 28, 2003, entitled "A Method for Developing Computational Models to Simulate the Host:Pathogen Interaction for Predictive Analysis of Disease States," which is hereby incorporated by reference in its entirety.

The present invention was made with government support under contract number N000140211031 awarded by the Defense Modeling and Simulation Office, Office of Naval Research. The government may have certain rights in the invention.

BACKGROUND THE OF THE INVENTION

In the wake of the September 2001 attacks and mailing of anthrax-laced envelopes, policymakers and the public have become increasingly more concerned with bioterrorism and the emergence of disease-causing organisms (pathogens). Currently, computational models indicate the social effect of such pathogens on a human population. However, to understand how these diseases work, and to effectively aid emergency responders in any epidemic or bioterrorist attacks, a model needs to be developed to predict what may happen to and within a person when a person becomes infected.

The onset, duration and outcome of a disease state or infection are complex dynamic processes that are mediated by interactive responses in which both the pathogen and the infected host play opposing roles. Pathogenic mechanisms are normally investigated using laboratory (in vitro) and live (in vivo) studies. The in vitro approach provides a means of investigating and testing the pathogenic mechanism using components of the host against which the pathogen demonstrates a virulence effect. In vivo studies, using natural hosts or genetic variants (mutants) that exhibit modified susceptibility, provide data on living systems.

Specific in vivo studies may include either outcome observations using the intact host or directed observation of host components after onset of the disease. The use of in vitro and in vivo studies, while providing a sound basis for the study of the host-pathogen interaction in the disease, each exhibit limitations. It is also frequently difficult to link the in vitro (mechanistic) studies to the in vivo observations. Furthermore, for some diseases (e.g., human diseases like anthrax) the lethal effects on the test subjects precludes in vivo studies that involve human (host) exposure to a disease-causing organism (pathogen). Nonetheless, the ability to understand and describe the host-pathogen interaction is a key factor in enabling practitioners to test the current intervention strategies and possibly devise strategies based on simulation studies.

Consequently, it would be desirable to have a model that can simulate what may happen to an individual when that individual is exposed to the pathogen or contracts a disease. Not only can such model facilitate a better understanding of the potential effects that a pathogen may have on a person, but it can also provide a time range as to how much time emergency responders or medical practitioners have to save an individual before life-threatening symptoms manifest. Moreover, such a model can help perform "what if" studies and develop testable hypotheses concerning a host-pathogen relationship. It would also be desirable to have a computational model to predict host-pathogen interactions that would ease concerns regarding animal testing. In addition, it would be desirable to have such a model to save hours of research time and costs.

BRIEF DESCRIPTION OF THE SEVERAL VIEWS OF THE DRAWINGS

The accompanying drawings, which are incorporated in and form a part of the specification, illustrate an embodiment of the present invention and, together with the description, serve to explain the principles of the invention.

FIG. 6 exemplifies steps that may occur in a discrete event simulation where aerosolized anthrax is the pathogen of interest and the host is exposed through inhalation.

FIG. 7 is a schematic diagram of an Anthrax Model.

FIG. 8 portrays an anthrax spore being phagocytized (engulfed) by an alveolar macrophage and then germinating and replicating in it.

FIG. 9 is a graph showing the appearance and number of various agents during the simulation period following deposition of anthrax spores in the lungs. Macrophage represents an alveolar macrophage. Spore represents an anthrax spore on the alveolar surface of the lungs. AMSpore represents an Alveolar Macorphage containing an anthrax apore (phagocytized spore). Phagosome represents an alveolar macrophage containing a spore localized in a phagosome. Cytoplasm represents an alveolar macrophage containing a germinated spore in its cytoplasm.

FIG. 10 is a graph showing the appearance and number of various agents (i.e., AMSpore—Alveolar Macrophage containing a spore; Phagosome—alveolar macrophage containing a spore localized in a phagosome; Cytoplasm—alveolar macrophage containing a germinated spore in its cytoplasm; Free Cell—alveolar macrophage containing germinated spores that have resulted in vegetative anthrax cells in the cytoplasm; Toxin—toxin produced in the alveolar macrophage by the vegetative cells) in the lymphatic system during the time course of the simulation. P2 represents panel 2 or the primary lymphatic panel.

FIG. 11 characterizes potential steps in a sample discrete event simulation. This figure is a flow diagram of an anthrax simulation, showing biological events and associated agents. Agent 1 represents an anthrax spore (pathogen). Agent 2 represents an alveolar macrophage (host). Agent 3 represents an alveolar macrophage containing a spore located in the phagosome (host-pathogen). Agent 4 represents an alveolar macrophage containing a phagosome/spore entity that is capable of germination (results in resolved infection). Agent 5 represents a vegetative anthrax cell (pathogen) in the cytoplasm of an alveolar macrophage (host cell).

DESCRIPTION OF THE INVENTION

The present invention provides methods and systems for developing models of the relationships that occur between a host and a pathogen, and other biological entities that establish associations with each other. The methods and systems apply agent-based simulation technology to the development of computer-based models, facilitating a systematic and analytical approach to relationships between biological entities. In particular, these methods and systems enable practitioners to explore "what if" scenarios and develop predictive data that may be used in experimental design and the testing of hypotheses of disease and other biological states.

The use of computer-based models to provide an in silico (computer-based) testing environment enable practitioners to study and analyze host-pathogen interactions, as well as other relationships between biological entities, and posit disease and other interventions, without having to perform all of the required experiments in vivo and/or in vitro. As shown in FIG. 1, practitioners may simulate hypotheses in an in silico model without testing them in vivo or in vitro. The simulated results generated may be validated against observations from in vivo and/or in vitro tests. Hence, the in silico approach may reduce the reliance on in vivo and/or in vitro models that are time-consuming, expensive, incomplete, difficult to interpret, or, in the case of animal or human studies, ethically problematic.

Figure 1:
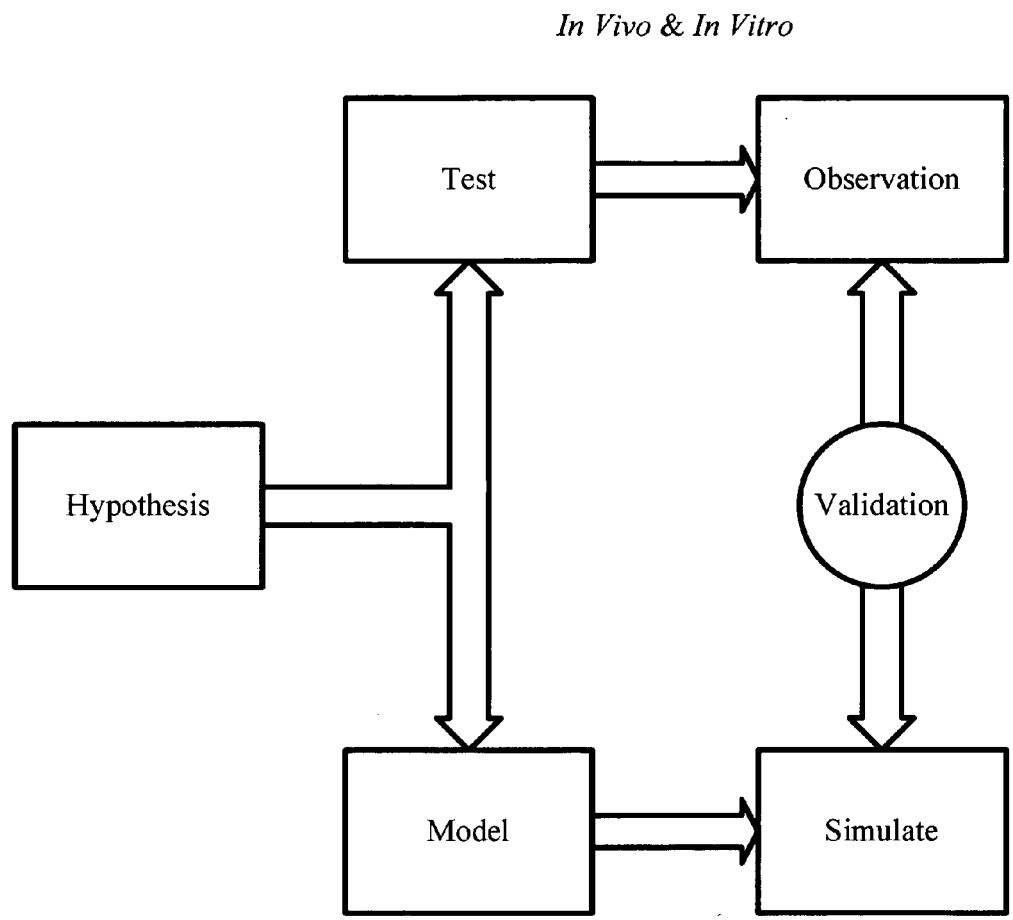
FIG. 1 is a flow diagram illustrating an experimental paradigm for linking in vivo and in vitro studies.
Figure 2:
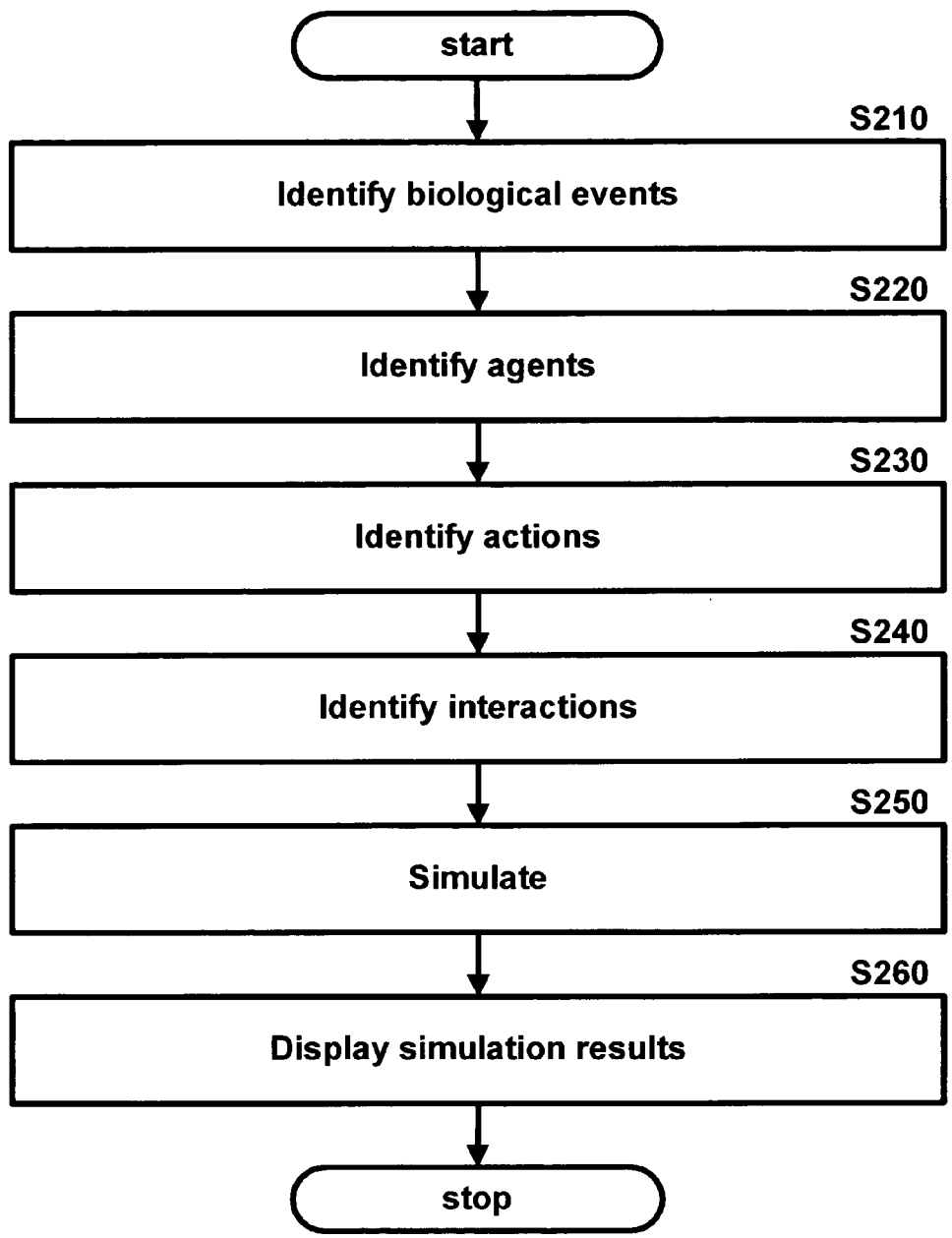
FIG. 2 exemplifies a method of developing an agent-based simulation system for a host-pathogen interaction.

In one embodiment (see, e.g., FIG. 2), the present invention includes a method of developing agent-based simulation systems capable of providing a systematic and analytical approach to a host-pathogen relationship. The method can comprise one or more of the following steps in any effective order: (a) identifying a plurality of biological events associated with a pathogen's invasion of a host, S210; (b) identifying for each biological event, at least one agent associated with the event (e.g., wherein the agent represents the host or a component thereof, and/or a pathogen or a pathogenic component thereof), S220; (c) describing the state for each agent and/or identifying at least one action for each agent, S230; (d) identifying at least one interaction between agents, S240; and/or (e) simulating a temporal course of the host-pathogen interaction using the plurality of biological events (S210), the agents associated with the biological events (S220), at least one identified action for each agent (S230) and at least one identified interaction between agents (S240), wherein the simulation is accomplished using an agent-based simulation system, S250; and (f) displaying the results of the simulation (see, e.g., FIGS. 9 and 10), S260. This method can be applied to any association between two or more biological entities.

One embodiment of the present invention involves identifying a plurality of biological events associated with a pathogen's invasion of a host, S210. A biological event indicates an occurrence that takes place during the association between two or more biological entities, such as between the host and pathogen, or different organisms in a symbiotic relationship. A sequence of biological events may describe the association, including events associated with the initiation of the relationship and how it progresses through its "normal" course of development. Where the relationship is between a host and a pathogen, the normal course of development refers to the possible scenarios when a host becomes infected with a pathogen, including the classic symptoms/events associated with pathogen infection (the "disease"), or when a host successfully is invaded, but "fights off" and/or resists the pathogen.

For a typical host-pathogen relationship, the biological events can include, for example, but are not limited to: the attachment of a pathogen to at least one host cell or surface; internalization; production of pathogenic encoded nucleic acids, proteins, lipids, carbohydrates, or combinations of thereof; the effect of said pathogenic components on the host; the host response including: innate, induced, or adaptive responses that can include, for example, but are not limited to: immune responses, chemokine production, and/or cytokine production; replication of at least one host or pathogen cell; cell destruction; and characterization of generic or disease-specific symptoms.

For each biological event, at least one agent associated with the biological event may be identified, S220. An agent may be described as the biological entity, itself, or any component of the biological entity that possesses a biological activity. Examples of agents include, but are not limited to, the biological entity (e.g., the host, pathogen, parasite, or symbiote); systems (such as the immune system, the digestive system, the lymphatic system, the parasympathetic or autonomic nervous system, etc.); organs; tissues; cells; organelles or other subcellular compartments; and biomolecules (such as polypeptides, nucleic acids, lipids, carbohydrates, etc). Agents can also refer to a specific form of the entity, such as any intermediate in its life cycle (e.g., a spore, vegetative cell, reproductive cell, seed, or infected cell); phagosome comprising a spore; or one or more biochemical moieties that result from the presence of the pathogen (e.g., a toxin, or inflammatory lipopolysaccharides), etc.

For the purposes of agent-based modeling, the agent can be embodied as a computer program that performs actions and interactions over an extended period of time, typically without continuous direct supervision or control. Actions and interactions are defined in more detail below, but generally indicate the behavior of an agent. An agent can be autonomous or at least semi-autonomous, indicating that it can perform actions and interactions without supervision or direct control, and can interact with another entity to obtain guidance or output results. Optionally, it can have a user interface.

The invention is not limited by the biological entities that are to be modeled. For example, the host can be any organism, both unicellular and multicellular, including animals, plants, protista or bacteria. Animals include, e.g., mammals, humans, livestock, cows, sheep, pigs, monkeys, dogs, cats, rats, arthropods, birds, reptiles, fish, insects, etc. A pathogenic agent can include, but is not limited to: bacteria; viruses; rickettsia; bacteriophages; subviral pathogens (such as prions and viroids); protista; monera; plants; algae; and fungi.

A state and an action for each agent can also be described and identified. A "state" is an internal data representation that can be used to describe the agent. For instance, the state of a pathogen can be described by its abilities; size or volume; agent; and/or other characteristics. For example, an anthrax spore, prior to its entry into the host, lacks motility, and therefore its state would be characterized as being immotile. An alveolar macrophage, however, has the ability to move across alveolar surfaces, and therefore its state can be described as being motile.

An "action" can be generally described as a biological activity or behavior of an agent, where the agent acts on the environment or another agent. At least one action for each agent can be identified, S230. For example, where the agent is a macrophage, actions of the macrophage include, but are not limited to: cell motility, such as its ability to move across the alveolar surface of the lung; ability to phagocytize foreign antigens; ability to recruit additional macrophages and other cells (e.g., neutrophils) and cellular factors (e.g., cytokines, chemokines) to the site of infection; and ability to manufacture and secrete cytokines, such as interleukins, interferons, tumor necrosis factor, and chemokines. Actions for any particular agent can be identified routinely, e.g., using textbooks and the available scientific literature.

An action can also be further characterized and described by its probability of occurrence, and/or the temporal sequence in which it can occur. For instance, after a macrophage phagocytizes (engulfs) a spore, the spore is isolated within the macrophage in a phagosome. In the development of an in silico model, the phagosome/spore entity can be described as a third agent. This third agent, itself—composed of a number of components that are not individually described but whose actions and interactions result in the described activity for the third agent—is capable of certain actions, including: the destruction of the spore by enzymes and other biomolecules (e.g., hydrogen peroxide) that are produced in, or, that are imported into the phagosome; germination of the spore in the phagosome; or, neutralization of the spore such that no further activity by the pathogen occurs. Each one of these actions has a certain probability of occurring and an attendant temporal component. A probability of occurrence can be determined by the appearance or existence of specified conditions in the system (e.g., concentrations of an enzyme, or enzymes or other biomolecules, that are present in the phagosome) and/or using mathematical formula (e.g., using the Michelis-Menton equation to determine the relative amounts of substrate and product, indicating how much of the substrate is digested by the enzyme) to determine stochastically whether the action will occur. The temporal component of agent action can also be used to specify when certain actions will occur. For instance, when data is available that a certain biological action takes a particular amount of time, this information can be used alone, or in combination with other information, to trigger the agent action so that it occurs in a specific temporal sequence.

In addition to actions, one or more interactions between agents may also be identified, S240. An interaction may be described as a reaction or response to an agent's action by another agent, i.e., an interaction occurs between at least two agents.

For example, consider the case where an agent is a cytokine, such as interleukin-1 (IL-1). IL-1, produced by mononuclear phagocytes, possesses a variety of actions, including, e.g., diffusing; binding to cell surface IL-1 receptors; increasing further synthesis of IL-1; inducing synthesis of interleukin-6 (IL-6); acting on endothelial cells to promote coagulation; increasing expression of surface molecules that mediate leukocyte adhesion; causing fever; inducing synthesis of acute phase plasma proteins; etc. The probability of whether a particular action of IL-1 will occur in the host can be determined by a number of factors, including, e.g., the concentration of IL-1, its ability to diffuse in the environment, and its receptor affinity. These factors can be expressed mathematically to determine the probability of an action occurring. For example, fever only occurs only when high concentrations of IL-1 and other, related biomolecules, are reached, which has a certain probability of taking place, e.g., depending on the number of macrophages present in a particular compartment.

Once IL-1 binds to its cognate receptor on a target cell, it elicits a signaling cascade that activates the cell and leads to its cellular response. This response can be described as an "interaction" because it is a result of the IL-1's "action" on the cell's surface receptors. After the interaction occurs, the cell agent, itself, may be capable of different actions, with each action again having a probability of occurring.

Interactions can occur between the host and pathogen, as well as other types of combinatorial interactions, including pathogen-pathogenic component, pathogenic component-pathogen, host-pathogenic component, pathogenic component-host, pathogen-pathogen and host-host.

Returning to the agent-based model, an agent can be embodied as a software computer program (e.g., using object oriented programming) that performs actions and interactions in accordance with specified rules. The actions can be represented, for instance, as one or more algorithms or mathematical equations that determine the probability that a particular event occurs, and describe the event with an associated temporal constant. With reference to the example above, a fever inducing action of a cytokine agent can be coded for in part by an equation that calculates the concentration of a cytokine in a particular compartment (e.g., based on diffusion, the number of activated macrophages present in the compartment, etc.). When the concentration in that compartment reaches a certain amount, the rule likely specifies that an "interaction" takes place between the cytokine and the body's compartment responsible for controlling body temperature (e.g., the hypothalamus), resulting in a rise in body temperature.

Using SWARM, MASON, or other agent-based modeling programs (see below), a spatial means for interaction of the agents can be imported, such as Grid2d and Swarm.space.Grid2dImpl, the interface and implementation of Grid2d. Grid2d is a simple 2d grid for storing objects and can be used to show the interaction of agents. The grid can be visually represented as a "panel." Any type of visual representation can be utilized, including graphical, mathematical (e.g., graphs, bars, or other quantitative representations), pictorial displays (e.g., where agents are pictorially depicted), etc. A graphical visual representation may include any Graphical User Interface, such as a web browser. The modeled association between the biological agents can be comprised of a plurality of panels (i.e., 2d grids), where each panel represents a different compartment (e.g., environment) where the agents interact with each other, and each panel can be linked together. Examples of panels include tissues (e.g., the alveolar surface of the lung), organs (e.g., liver, spleen), and discrete systems (e.g., the lymphatic system or circulatory system).

Various parameters can also be set for the particular "environment" in which the agents operate (i.e., act or interact), such as the lung or other organ or tissue. For example, parameters can control the spatial dimensions of the lungs and lympatic system being modeled. Similarly, parameters can specify the capacity of organs such as the liver and spleen.

The term "identifying" as used herein indicates that recited information (e.g., biological event, action, interaction, feedback loop, etc.) is retrieved from a source. Thus, it can also be described as a "retrieving" step. Any source, or means of retrieving information from the source, can be utilized without limitation. Examples of sources include, e.g., journal references, textbooks, unpublished materials, encyclopedias, information available on the World Wide Web, technical reports, patents, oral exchanges, etc. In essence, for instance, information describing how an alveolar macrophage phagocytizes an anthrax spore may be obtained from the World Wide Web. Additionally, information can also be organized into computerized databases, which are then searched or mined for the desired information.

Furthermore, the temporal course of association between the biological entities (e.g., between a host and a pathogen) may include specific interventions or treatments that can be assessed for their influence on the association. For example, treatments can influence the outcome by negatively impacting the capacity of the pathogen to affect the host, by inducing responses in the host that negatively impact the pathogen, or by removal or destruction of the pathogen. Examples of interventions include, e.g., antibiotics; vaccines and other antigen preparations that induce an immune response in the host; interferons; neutralizing antibodies (such as anti-TNF); interfering viruses; agents that modulate any pathway involved in pathogenicity; radiation; etc. Thus, methods of the present invention can further comprise: identifying an intervention having at least one action, and using said intervention in simulating the temporal course of said host-pathogen association. The intervention may also act by interfering with the pathogenic actions induced by the action of components of the pathogen on the host. The term "intervention" generally means any agent or treatment modality that is utilized to influence the association between the two biological entities, whether such intervention is effective or not. The intervention, itself, can be modeled as an agent having one or more actions. For instance, if the agent is a vaccine, its action can be: to induce antibodies capable of neutralizing one or more antigens present in the pathogen. Some interventions that are included in this definition act by replacing biomolecules that are depleted during the course of the disease. For example, replacement of sugars, electrolytes, and other fluids are interventions that help to maintain homeostasis during many disease states of humans—these interventions can maintain host functions and influence the outcome of the disease.

One or more of the above-mentioned identifications may be used to construct an agent-based simulation system of the temporal course of the host-pathogen relationship, S250. Such simulation systems can then be executed by running them on an agent-based simulation system, such as SWARM by the Swarm Development Group or Multi-Agent Simulator Of Neighborhoods "MASON," which is a joint effort between George Mason University's (GMU) Evolutionary Computation Laboratory (ECLab) and the GMU Center for Social Complexity. These publicly available and open source systems are hereby incorporated by reference in their entirety. Agent-based modeling is well known in the art, see, e.g, Berry, Brian L., L. Douglas Kiel, and Euel Elliott, eds. 2002. *Adaptive Agents, Intelligence and Emergent Human Organization: Capturing Complexity Through Agent-Based Modeling.* Vol. 99, *Proceedings of the National Academy of Sciences*: National Academy of Sciences; Gerkey, Brian, Richard T. Vaughan, and Andrew Howard. 2003. "The Player/Stage Project: Tools for Multi-Robot and Distributed Sensor Systems" *Proceedings of the* 11*th International Conference on Advanced Robotics,* 317-323; Macal, Charles M., and David Sallach, eds. 2000. *Proceedings of the Workshop on Agent Simulation: Applications, Models, and Tools*. Chicago: Social Science Research Computation, The University of Chicago, and Decision & Information Sciences Division, Argonne National Laboratory; Sallach, David, and Thomas Wolsko, eds. 2001. *Proceedings of the Workshop on Simulation of Social Agents: Architectures and Institutions*. Chicago, Ill.: Social Science Research Computation, The University of Chicago, and Decision and Information Sciences Division, Argonne National Laboratory.

Figure 3:
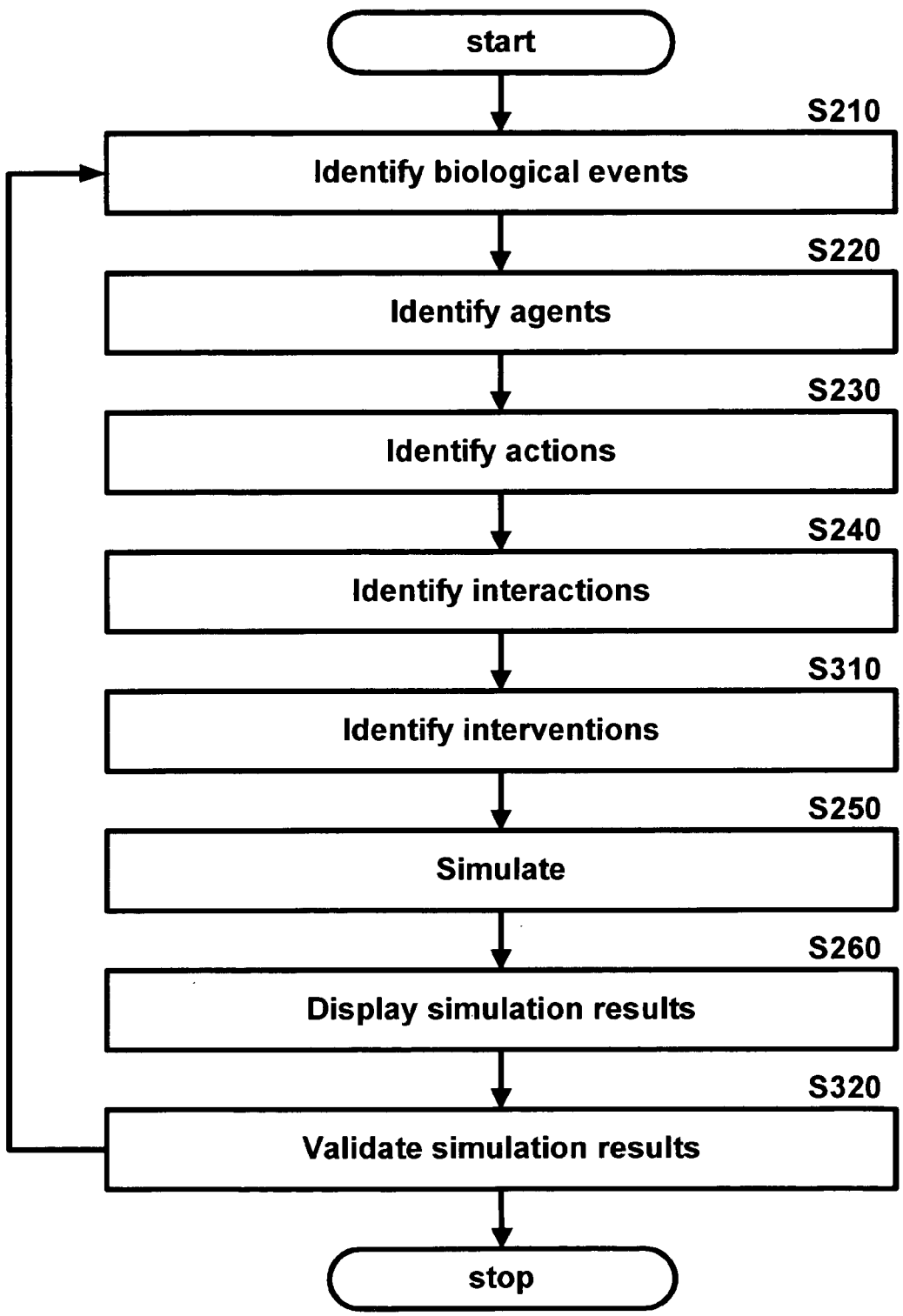
FIG. 3 shows another method of developing an agent-based simulation system for a host-pathogen interaction.

Methods of the present invention can further comprise validating the simulated results, S320, as indicated in FIG. 3. The addition of a validating mechanism, such as a validator 520 can be used to compare the result's precision, accuracy or both to known data. Parameters in biological systems can correlate with known data under certain environmental conditions. The present invention may use a validating mechanism to, for example, demand that results fall within a particular range of known data based upon in vitro and in vivo conditions and observations. Once results are generated, the validating mechanism may compare the simulated results to these conditions and observations. If the simulated results do not fall within a desired range, then the model may demand the model user to change parameters. The model may even stop simulating or display an error message. Validation can be implemented at any step of the methods.

Yet another embodiment includes allowing the in silico model to be modifiable. Because disease states tend not to be constant, introducing variations in an agent's state, perception or behavior at any stage of the simulation would be beneficial to more accurately represent the actions and interactions within an agent. Likewise, a modifiable model may also facilitate the prediction of outcomes of introduced variations.

Figure 4:
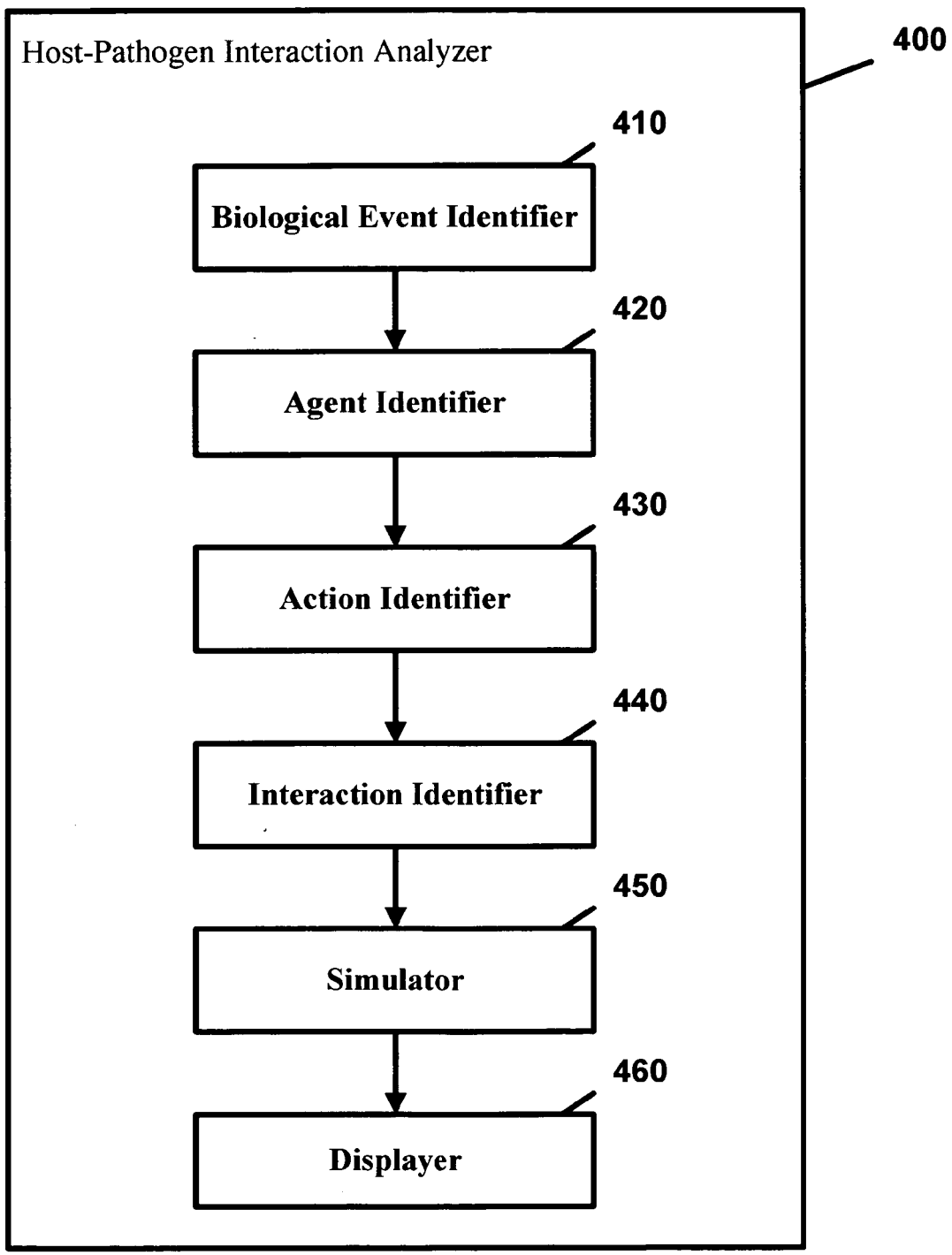
FIG. 4 is an example of a system of implementing an agent-based simulation system for a host-pathogen interaction.
Figure 5:
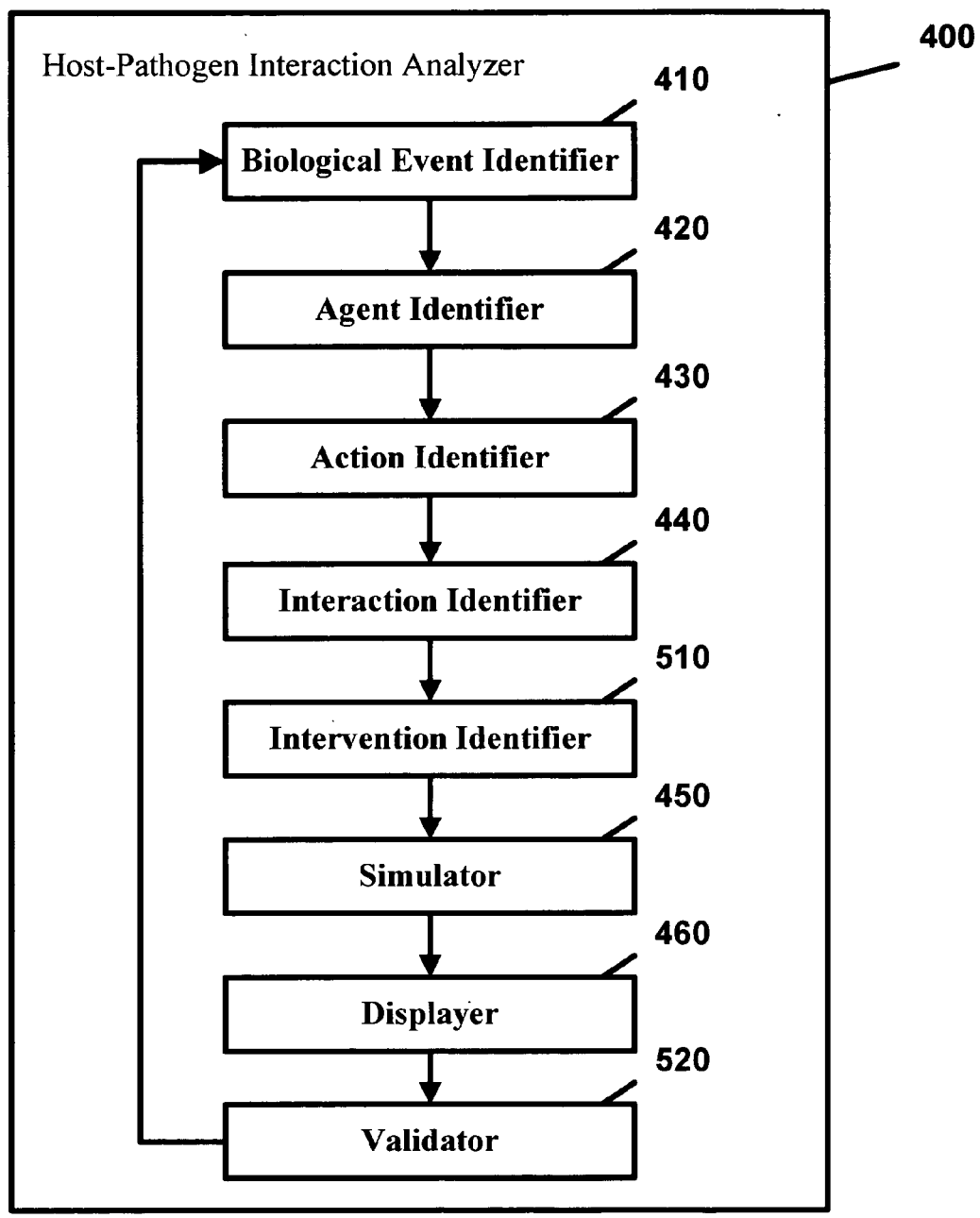
FIG. 5 depicts another system of implementing an agent-based simulation system for a host-pathogen interaction.

Methods of the present invention may even be incorporated into systems. Referring to FIGS. 4 and 5, a system may comprise of a host-pathogen interaction analyzer, 400. For the in silico to function, this analyzer 400 may contain a biological entity identifier, 410, an agent identifier, 420, an action identifier, 430, an interaction identifier, 440, a simulator, 450, and a displayer, 460. The biological entity identifier 410 may be used to identify a plurality of biological events associated with a host-pathogen interaction. The agent identifier 420 may be used to identify an agent for each biological event identified. The action identifier 430 and an interaction identifier 440 may be used to identify actions and interactions, respectively. The "identifier" functions can be accomplished manually, or using computerized algorithms that search databases, or mine sources (e.g., textbooks, journals, textbooks) for the desired information. Having identified one or more of these components of the in silico model, a simulator 450 may be used to simulate a temporal course of the host-pathogen interaction. Results from the simulator may be displayed (see, e.g., FIGS. 9 and 10) using a displayer 460.

As another embodiment, the system may also house a validator 520. Reflected in FIG. 5, the validator 520 may use known data, such as observations from animal and laboratory testing, to validate simulated results. Additionally, the system may also incorporate a feedback loop to allow the simulation to continuously insert output as input for the system until an end is met. The feedback loop merely illustrates one embodiment of where output may be reinserted into the system. Furthermore, the system may be modifiable. At any stage of the simulation, variations in an agent's state, perception or behavior may be introduced in the host-pathogen interaction analyzer 400. In turn, the system may allow the predictions of outcomes of these introduced variations.

The system can also comprise an intervention identifier 510. The intervention identifier 510 can be used to identify an intervention having at least one action. The identifier intervention, in turn, can be used in simulating a temporal course of a host-pathogen association.

The system can further comprise a dataset collector which is responsible for retrieving information about the agents and other aspects of the biological association which are useful for developing the simulation system. A dataset collector can be a computer robot that seeks information available in a data space, such as the World Wide Web. It can be used to create a database upon which information is further extracted about the actions and interactions of agents.

Yet, the system may further comprise a series of linked panels. These panels may provide a visual representation of the host. Any type of visual representation can be utilized, including graphical, mathematical (e.g., graphs, bars, or other quantitative representations), pictorial displays (e.g., where agents are pictorially depicted), etc. The modeled association between the biological agents can be comprised of a plurality of panels (i.e., 2d grids, as described above), where each panel represents a different compartment (e.g., environment) where the agents interact with each other. These panels include, for example, panels for tissues, organs and discrete systems.

For demonstrative purposes, the present invention uses a human as the host and anthrax as the pathogen in the in silico model (Anthrax Model). The principles that guided the development of the anthrax application can be applied to other host-pathogen associations, as well as other associations between biological entities. The invention may further enable those skilled in the art to develop computational models in silico that can provide systematic and analytical approaches for predicting the onset, duration and outcome of a host exposed to one or more disease-causing agents, as well as the impact of interventions on the onset, duration, severity and outcome of the infection or infections.

The use of in silico models can provide quantitative predictions concerning a host-pathogen interaction through inputs that are typically based on physiological assumptions and measurable parameters. As one embodiment of the invention, the Anthrax Model permits a computational representation of a complex system involving the host and the disease-causing organism. In this embodiment, which uses computer programs developed for "Agent Based Modeling," the Anthrax Model allows the user to explain or predict the dynamics of macroscopic properties, including the disease status and patient symptoms, from rules that operate at the microscopic level of systems interacting with each other and with their local environments.

As indicated above, any relationship between a host and a pathogen can be modeled in accordance with the present invention. These include, e.g., *Yersinia pestis* (Plague); *Francisella tularensis* (Tularemia); *Legionella* (Legionnaires disease); *Bordetella pertussis* (Whooping cough); *Mycobacterium tuberculosis* (Tuberculosis); *Salmonella enterica Typhi* (Typhoid fever); *Rickettsia prowazkeii* (Typhus); *Vibrio cholerae* (Cholera); *Streptococcus pneumoniae* (Meningitis); *Neisseria meningitidis* (Meningitis); Bacteria Cutaneous diseases (e.g., MRSA, VRSA, Leprosy, Anthrax, Tularemia, and Lyme disease); bacterial toxin-associated diseases (e.g., Tetanus, Botulism, and Listeriosis); viral aerosol diseases (e.g., Smallpox, Viral pneumonia, and Viral meningitis); viral non-aerosol diseases (e.g., Dengue Fever, Measles, Chickenpox, and Mumps); viral transmissible diseases (e.g., Herpes, Papilloma virus, Ebola, and Marburg); parasitic diseases (e.g., Malaria, and Leishmaniasis); and chronic diseases (e.g., diabetes and cancer). For cancer and other diseases in which either the pathogen is unknown or where there is no extrinsic pathogen, the aberrant cell (e.g., the cancer cell in cancer; the inflamed neuronal cell in MS; the pancreatic cell in diabetes, etc) can be modeled as the pathogen.

EXAMPLE

The Anthrax Model

Figure 6:
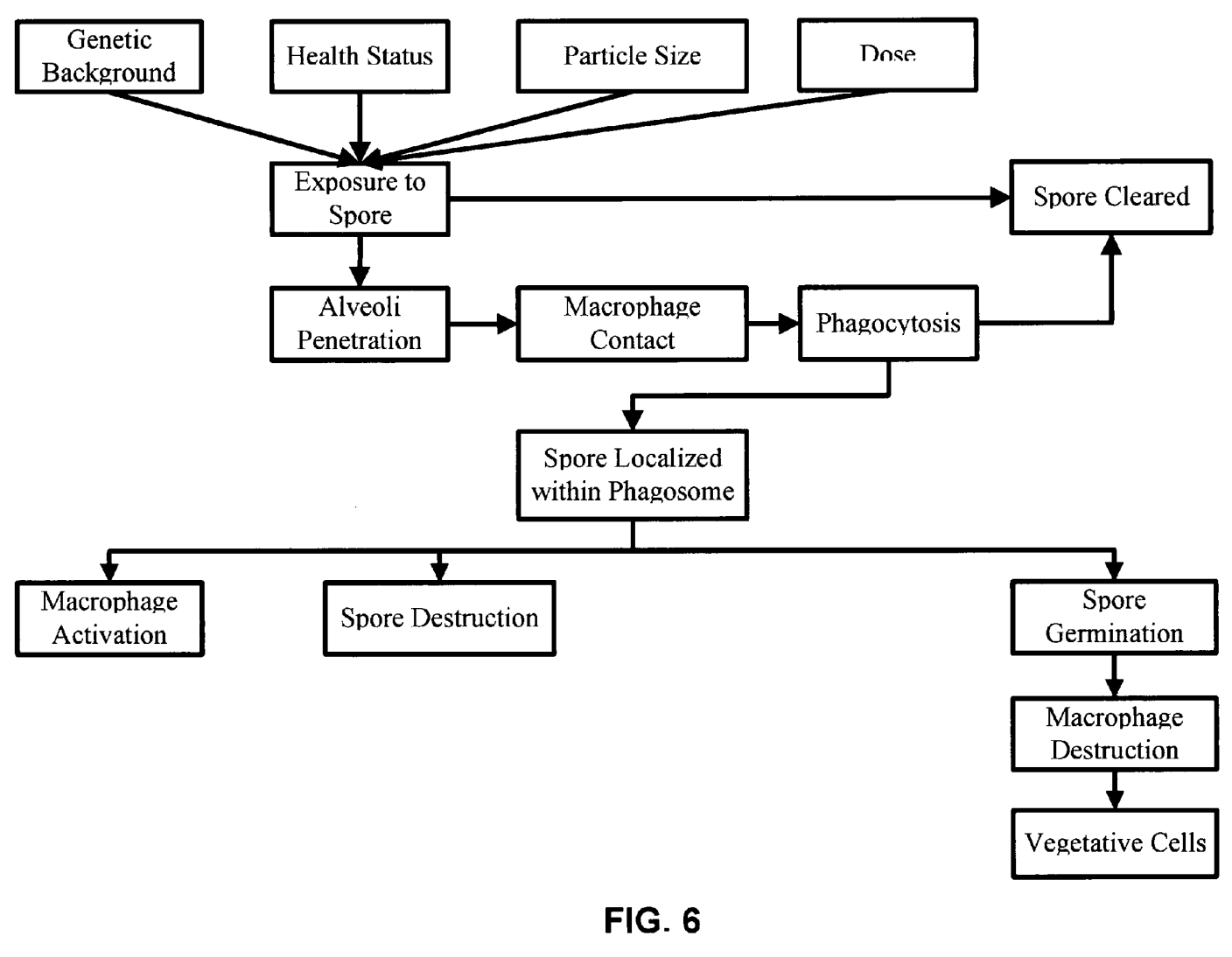

An agent-based anthrax model provides an alternative method for undertaking studies that cannot be performed on humans for ethical reasons, as well as studies that lack relevance if performed on animal species serving as human surrogates. FIG. 6 exemplifies steps that that may occur in a discrete event simulation where aerosolized anthrax is the pathogen of interest and the host is exposed through inhalation. The Anthrax Model may begin by retrieving information about the host and pathogen. FIG. 6 exemplifies this retrieval by gathering information regarding the genetic background and the health status and susceptibility of the host to the pathogen of interest, as well as about the particle size and the exposure dose of the anthrax spores (pathogen). Once retrieved, the information may be set as parameters for the simulation. Simulation may begin by exposing in silico the host (human) to the pathogen (anthrax spores). Once exposed, the spore may either be cleared (e.g., through respiration and other mechanical processes that operate in the airways and lungs of the host) or penetrate the lungs to the level of the alveoli. If it penetrates the alveoli, the spores can be deposited on the alveolar surface. The alveolar surface forms the initial "host environment" for the model and can be represented as a "panel." Macrophages (host cells) that are present on the alveolar surface (alveolar macrophages) exhibit a motile function, and thus can contact the spores. Contact between the alveolar macrophage (host) and the anthrax spore (pathogen) can result in the spore being phagocytized (engulfed) by the alveolar macrophage. The engulfed spore can then be localized within the alveolar macrophage in a discrete location called a phagosome. The action of phagocytosis can also lead to macrophage activation. In this state, the alveolar macrophage can generate chemical signals that are released and that have biological functions that can include localized and generalized responses by the host. Such responses include, but are not limited to, a rise in temperature, activation of the innate and inflammatory responses, and the attraction of other host cells to the site where phagocytosis has occurred. The fate of the anthrax spore that is localized in the phagosome within the alveolar macrophage can be described as, and may result in, the destruction of the spore or spore germination. The germination of the spore can lead to destruction of the alveolar macrophage and release of anthrax organisms in the form of vegetative (live) cells. In either case, after phagocytosis, the alveolar macrophage can continue exhibiting a motile function and migrate across the alveolar surface to a series of ducts that eventually leads to translocation of the alveolar macrophage from the alveolar surface of the lung into the primary lymph nodes that are associated with the lungs. The lymph nodes function to remove fluids (lymph), including lymph fluid containing alveolar macrophages, from the alveolar surface. The aerosol challenge from anthrax spores can thus result in the primary lymph nodes providing the portal for entry of the anthrax pathogen into the lymphatic system of the host, and form the basis for the disease state that is caused by inhalational anthrax infection.

Figure 7:
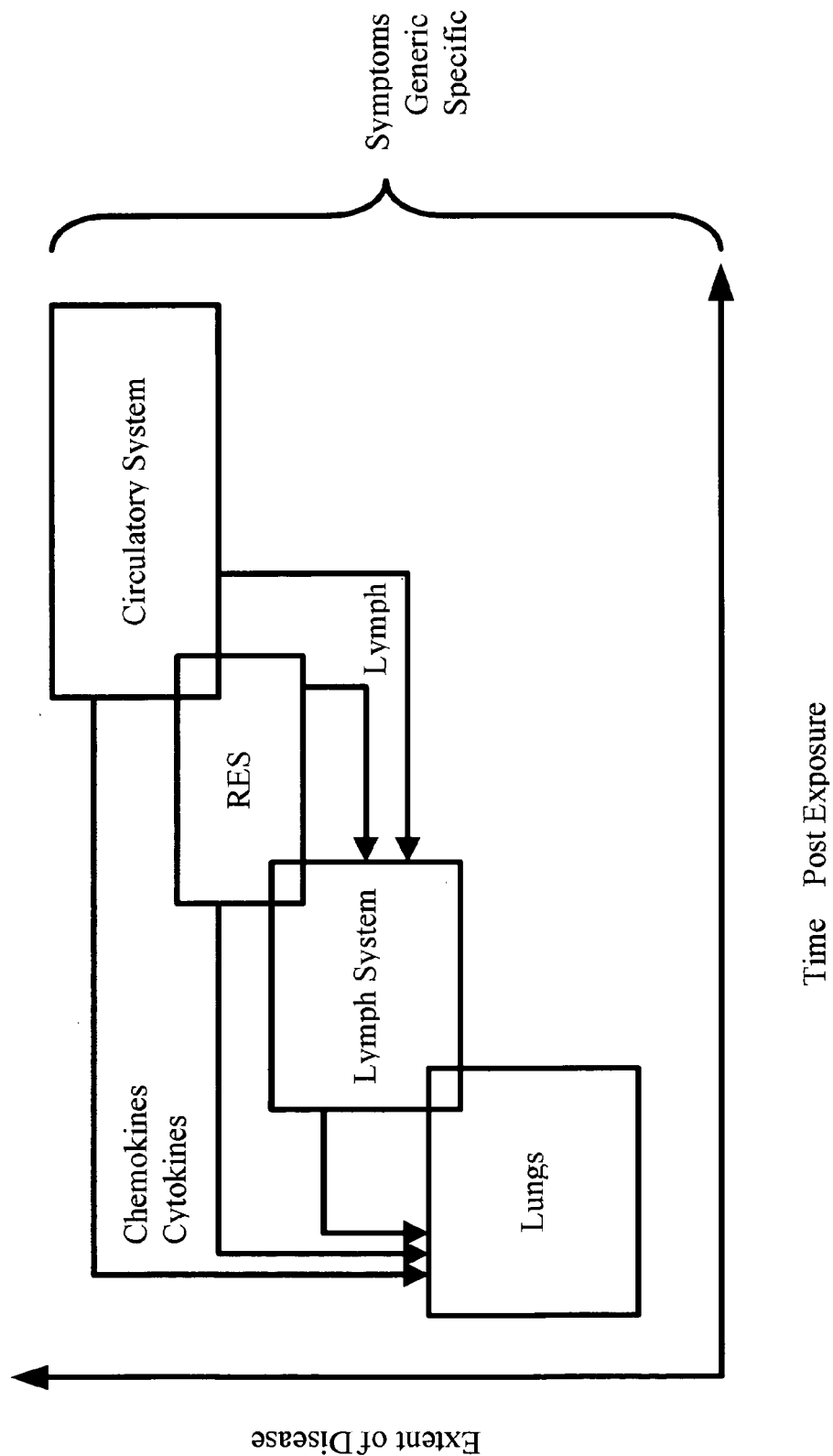

FIG. 7 shows a schematic diagram of the Anthrax Model. As a further explanation of how exposure to anthrax spores may affect the host, this figure illustrates which host components (e.g., tissues, organs, systems) can become affected after inhalational exposure to anthrax spores. The lungs are the primary site of infection. As the disease spreads, infection moves into the lymphatic system, into the organs that comprise the reticulo-endothelial system (RES) (e.g., liver, spleen, kidneys) and into the circulatory system. Throughout the extent and time of exposure, both generic symptoms (e.g., fever, fatigue, cough) and specific symptoms (e.g., widening of the mediastinal space) may be manifested by the host. As previously described at the systematic, cellular and subcellular levels, there can be significant feedback loops in operation. These loops can be built into the model and can represent important components of the disease state and impact of the host-pathogen interaction. The feedback loops include specific host fluids (e.g., lymph), generalized biochemicals (e.g., chemokines, cytokines), effectors of the inflammatory and immune responses (e.g., Interleukins, Interferons, Tumor Necrosis Factor), and the adaptive immune response (e.g., immunoglobins).

In vivo models have been developed and widely used to study anthrax, but they have varying relevance to the clinical (human) experience. The "gold standard" in vivo model for anthrax is a primate model. The limited availability, cost and difficulty in performing studies on these animals represent a significant obstacle to the development of improved treatments for the disease. Other in vivo models may be easier to perform but often need to be accurately linked to the human experience if they are to be considered to be clinically relevant. Methods for developing treatments and guiding animal studies are needed to close the gap between the threat and ability to respond. The in silico approach provides a novel solution to these problems, exemplifying the value of computational models to simulate the host-pathogen interaction for predictive analysis of the disease anthrax.

An agent-based simulation system for the anthrax disease state in humans can involve identifying data and other information about the pathogen and the disease. Sources for this data can include, but are not limited to, reports of human anthrax (e.g., cutaneous, inhalation, etc.); reports of human exposure to anthrax that did not lead to development of the disease; and relevant animal data, such as primate data involved in challenge studies with anthrax. Additionally, literature references, textbooks, online databases, etc., can be used to extract information about the host and pathogen systems, e.g., to identify actions and interactions.

In addition to the data available on the "whole body" in vivo exposure to anthrax, there are other sources of data that can be used to provide information on the disease at the mechanistic level. Such information includes, e.g., studies performed to assess the influence of particle-sized infectious doses; evaluations of the mechanisms by which the infecting agent enters the body; and issues relating to the germination and release of the germinated spore from the macrophage. There is also a large body of data concerning the toxins that are produced by anthrax, and their role in the pathogenesis of the disease. Data from these mechanistic studies can be utilized in the Anthrax Model as appropriate.

Figure 8:
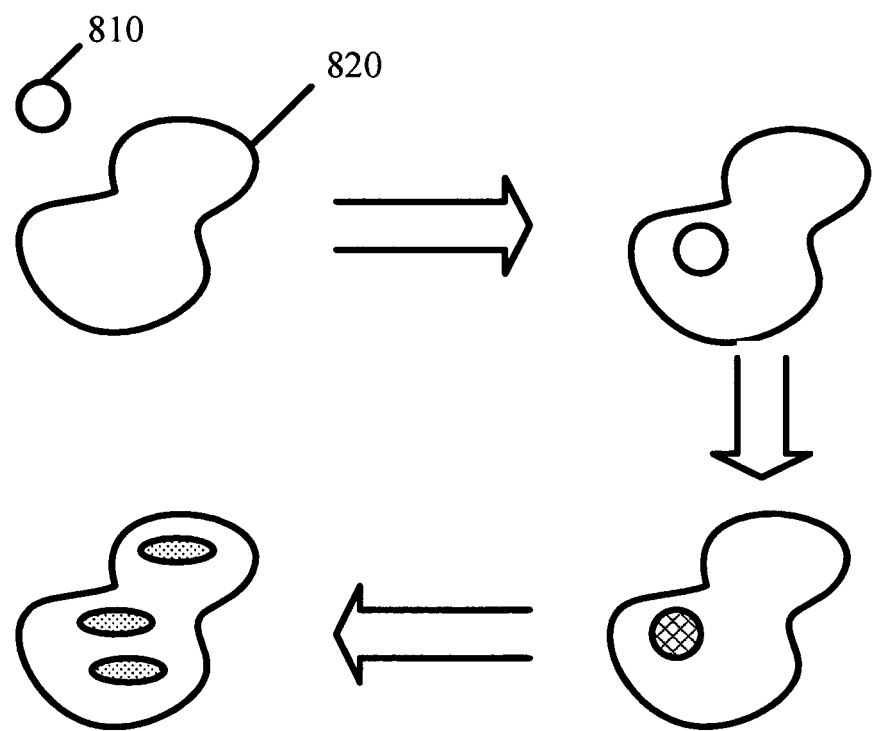

Discrete biological events can also be identified for the anthrax disease state. Biological events may include, e.g., but are not limited to, the attachment of a pathogen to at least one host cell or surface; internalization; production of the pathogenic encoded nucleic acids, proteins, lipids, carbohydrates or combinations thereof; the effect of said pathogenic components on a host; the host response including: innate, induced or adaptive responses that can include, for example, but are not limited to: immune responses, chemokine production, and/or cytokine production; replication of at least one host or pathogen cell; cell destruction; and characterization of symptoms. For example, FIG. 8 illustrates an spore 810 coming into contact with an alveolar macrophage 820. Contact between the alveolar macrophage (host) and the anthrax spore (pathogen) can result in the spore being phagocytized (engulfed) by the alveolar macrophage. The engulfed spore can then be localized within the alveolar macrophage in a discrete location called a phagosome. Once events are identified, the agents involved in these events are modeled bottom-up by further associating the agents with actions and interactions as described previously.

This information—events, agent, actions, and interactions—can provide the basis for an agent-based computer simulation. The simulation can be used to assess what happens during a biological event and what happens at the end state when the biological event is completed. The outcome of the biological event can be linked to subsequent biological events in a simple network model.

The use of an agent-based modeling approach in developing the Anthrax Model allows for the modeling of components (agents) from both the host and the pathogen, and the expression of the expression of their relationship in terms of individual actions, interactions and results of either, in terms of modifying the agent, other agents or the environment in which the agents are modeled. This aspect facilitates the explanation or prediction of the dynamics of macroscopic properties of the system, including the disease status and patient symptoms, from rules that operate at the microscopic level of systems interacting with each other and with their local environments.

Figure 9:
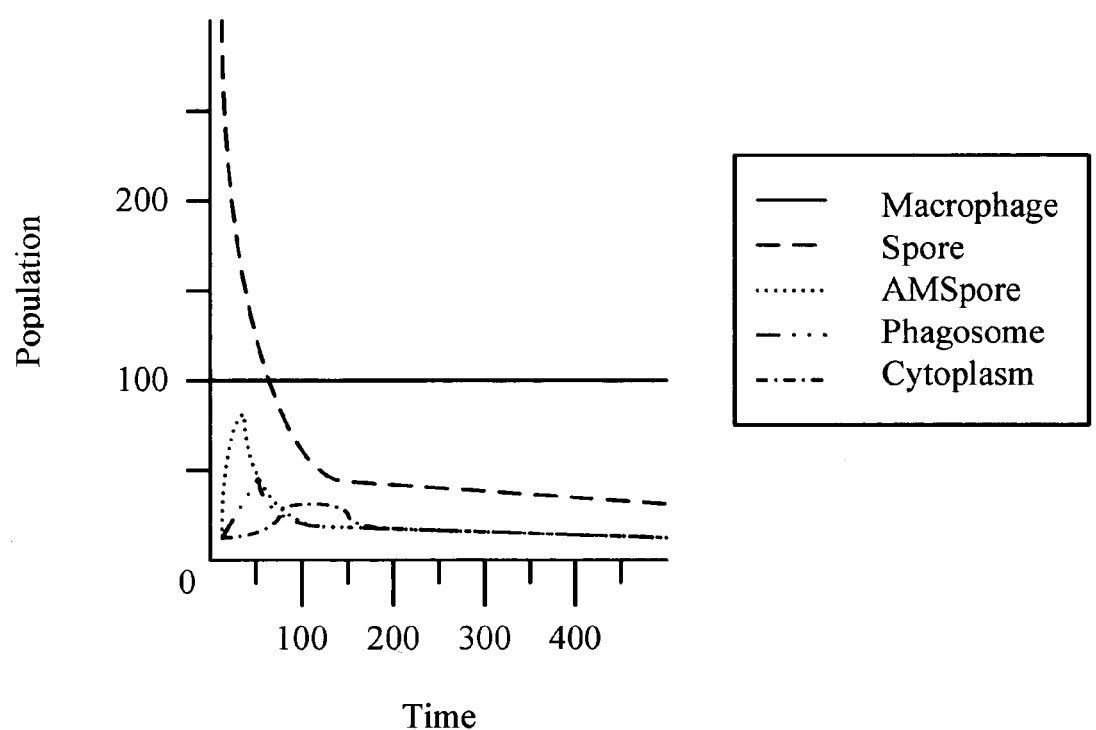
Figure 10:
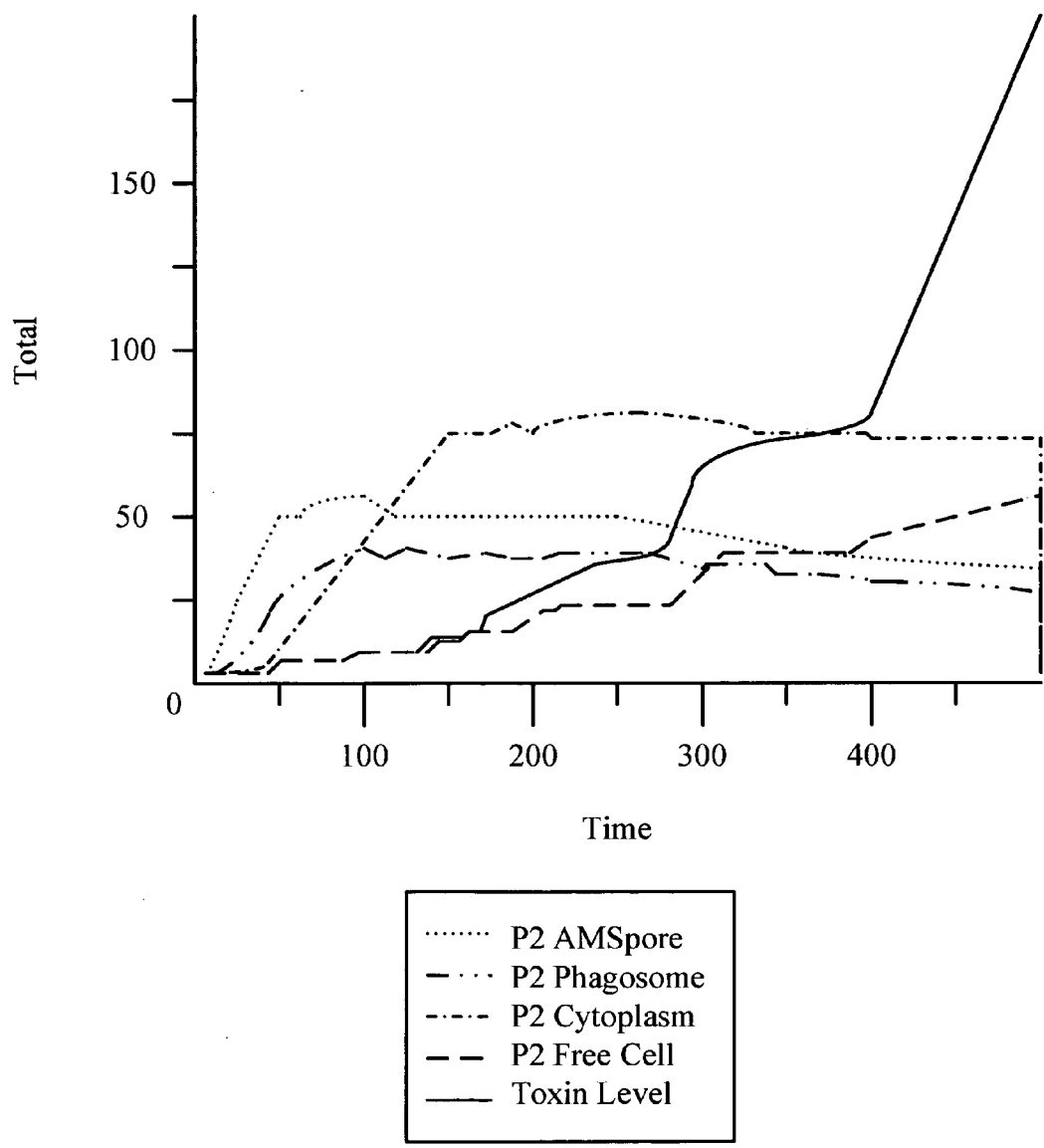

The model can incorporate any of the widely available features in SWARM, MASON, or other agent-based modeling approaches. A Graphical User Interface (GUI), such as a web browser, may be used to provide a graphical representation of the components of the Anthrax Model. The following figures illustrate line graphs showing the appearance and number of various agents during the simulation period following the deposition of anthrax spores in a particular part of the body. FIG. 9 displays this comparison in the lungs, which is a common primary infection site. FIG. 10 displays this comparison in the lymphatic system, which is a common secondary infection site.

The model may further comprise a series of linked panels that represent the host organs and tissues (e.g., lungs and lymphatic system) involved with human anthrax (see FIG. 7). Within the panels, the modeled agents represent host organelles (e.g., phagosome) and the pathogen (e.g., anthrax spore) or pathogen components (e.g., toxin). For example, in the panel representing the alveolar region of the host lung, the agents can include alveolar macrophages (host) and anthrax spores (pathogen). The model can then be used to simulate the actions of these two agents within the host environment (alveolar region of the human lung). Specific actions on the part of the agents (e.g., motility and chemotaxis of the alveolar macrophage) or interactions between agents (e.g., phagocytosis of the anthrax spore by the alveolar macrophage) can be further modeled using mathematical equations from the computational modeling software that specify the relationships. These relationships may be represented by specific graphical representations. The mathematical relationships in the Anthrax Model can be derived from the discrete event simulation and from detailed analysis of the published results from in vitro and in vivo studies on the host-pathogen interaction.

In addition, the Anthrax Model can also have a validating mechanism 520 to validate the simulated results. Such mechanism can be used to compare the result's precision, accuracy or both to known anthrax data, which may be obtained from a multitude of resources (e.g., in vivo studies, in vitro studies, the World Wide Web, encyclopedias, journals, etc.).

Furthermore, the Anthrax Model can be modified at any stage to account for variations in an agent's state, perception or behavior at any stage of the simulation and, as such, allow for exploration of predictive scenarios. From the standpoint of understanding the complex features of human anthrax disease, the Anthrax Model permits quantitative predictions through inputs to the model that may be based on physiological functions and measurable parameters.

Referring to FIG. 11, a flow diagram represents a way of characterizing potential steps in a sample discrete event simulation of the Anthrax Model. This figure shows biological events and associated agents, where Agent 1 represents an anthrax spore (pathogen) and Agent 2 represents an alveolar macrophage (host). If Agent 1 comes in contact with Agent 2, then the spore may be phagocytized (engulfed and internalized within the alveolar macrophage). The spore can germinate, creating Agent 3, where Agent 3 represents a phagosome/germinated spore entity. If Agent 1 does not come in contact with Agent 2, the spore may be cleared from the lung (host) by physiological processes or remain in a dormant state. This clearance may lead to a subsequent repeat of the cycle at a later time with Agent 1 coming into contact with Agent 2. If the phagosome/spore entity does germinate, then it may lead to the destruction of the phagosome and release of a vegetative anthrax cell (Agent 5) into the cytoplasm of a host cell (alveolar macrophage). If the phagosome/spore entity does not germinate, then the phagosome/spore entity can result in the destruction or inactivation of the spore. This entity may be viewed as Agent 4. If a sufficient amount of the anthrax spores (pathogen) are destroyed/inactivated, then the infection may be resolved.

Thus, the Anthrax Model can provide an in silico link between the in vitro laboratory studies and the in vivo models. This capability has many practical applications, including: permitting the development and testing of hypotheses concerning human anthrax from in vitro laboratory studies and the in vivo models; reducing the current reliance on animal models; providing a basis for defining potential approaches to clinical intervention and treatment of anthrax in humans; and providing "virtual victims" to access the impact of anthrax in populations with varying susceptibilities.

The Anthrax Model exemplifies the way in which in silico agent-based models provides quantitative predictions concerning the host-pathogen interaction through inputs that are based on physiological assumptions and measurable parameters. In this example, the use of computer programs that were developed for "Agent-Based Modeling" enables the user to explain or predict the dynamics of macroscopic properties, including the disease status and patient symptoms, from rules that operate at the microscopic level of systems interacting with each other and with their local environments.

The foregoing descriptions of the preferred embodiments of the present invention have been presented for purposes of illustration and description. They are not intended to be exhaustive or to limit the invention to the precise forms disclosed, and obviously many modifications and variations are possible in light of the above teaching. The illustrated embodiments were chosen and described in order to best explain the principles of the invention and its practical application to thereby enable others skilled in the art to best utilize the invention in various embodiments and with various modifications as are suited to the particular use contemplated.

What is claimed is:

1. A predictive data development method that models host-pathogen interactions based on simulated actions, interactions and at least one feedback loop executed by a suitably programmed computer, said method comprising:
    a) identifying a plurality of biological events associated with said interactions;
    b) identifying for each of said biological events at least one host agent and at least one pathogen agent associated with said events;
    c) identifying at least one action for each of said at least one host agent and said pathogen agent;
    d) identifying at least one interaction between said at least one host agent and said pathogen agent in a plurality of grids representative of said host;
    e) simulating a temporal course of said modeling using said plurality of biological events, said at least one host agent and said pathogen agent, said at least one action, and said at least one interaction; and
    f) displaying results of said simulating by graphically transforming the results into displays that indicate the predicted outcome of the host-pathogen interaction in a time-phased display; and
    g) wherein said simulating is accomplished using an agent-based simulation system comprising:
        1) bidirectional flow at least of at least one of said at least one pathogen agent between at least two of said plurality of grids; and
        2) at least one feedback loop representative at least of at least one said at least one interaction that applies output of at least one of said plurality of grids of the simulation as input for at least another of said plurality of grids of the simulation until an end is met, the end including at least one of:
            i) the host overcomes the pathogen;
            ii) the pathogen overcomes the host; and
            iii) the host becomes tolerant of the pathogen.

2. The predictive data development method according to claim 1, further comprising:
    identifying an intervention having said at least one action, and using said intervention in simulating said temporal course of said host-pathogen interactions.

3. The predictive data development method according to claim 1, further comprising:
    retrieving information describing said at least one action of at least one of said at least one agent from a source.

4. The predictive data development method according to claim 1, further comprising:
    setting parameters for at least one environment in said simulating where said at least one agent operates.

5. The predictive data development method according to claim 1, wherein said host agent is a cell of said host.

6. The predictive data development method according to claim 1, wherein said pathogen agent is an intermediate in a life cycle of said pathogen.

7. A method according to claim 1, wherein said agent is a polypeptide of said pathogen.

8. The predictive data development method according to claim 1, wherein said pathogen is a bacteria.

9. The predictive data development method according to claim 1, wherein said action is said at least one agent acting on the environment.

10. The predictive data development method according to claim 1, wherein said action is said at least one agent acting on another agent.

11. The predictive data development method according to claim 1, wherein said host is a human and said pathogen agent is anthrax.

12. The predictive data development method according to claim 1, further comprising validating said results.

13. The predictive data development method according to claim 1, further comprising a series of linked panels, capable of providing a graphical representation or mathematical representation of said host, wherein said series of linked panels comprise at least one of said at least one agent that is modeled.

14. A predictive data development method that models host-pathogen interactions based on simulated actions, interactions and at least one feedback loop executed by a suitably programmed computer, the method comprising:
    a) simulating a temporal course of said modeling using:
        1) a plurality of biological events associated with said interactions;
        2) at least one host agent and at least one pathogen agent associated with said biological events;
        3) at least one action associated with each of said at least one host agent and said pathogen agent; and
        4) at least one interaction between said at least one host agent and said pathogen agent in a plurality of grids representative of said host; and
    b) displaying results of said simulating by graphically transforming the results into displays that indicate the predicted outcome of the host-pathogen interaction in a time-phased display; and
    c) wherein said simulating is accomplished using an agent-based simulation system comprising:

1) bidirectional flow at least of at least one of said at least one pathogen agent between at least two of said plurality of grids; and
2) at least one feedback loop representative at least of at least one said at least one interaction that applies output of at least one of said plurality of grids of the simulation as input for at least another of said plurality of grids of the simulation until an end is met, the end including at least one of:
   i) the host overcomes the pathogen;
   ii) the pathogen overcomes the host; and
   iii) the host becomes tolerant of the pathogen.

15. An agent based simulation system comprising a host-pathogen interaction analyzer that provides a systematic and analytical approach for modeling host-pathogen interactions based on simulated actions, interactions and at least one feedback loop, the analyzer comprising:
   a) a biological event identifier, capable of identifying a plurality of biological events associated with said interactions;
   b) an agent identifier, capable of identifying for each of said biological events, at least one host agent and at least one pathogen agent
   c) an action identifier, capable of identifying at least one action for each of said at least one host agent and said pathogen agent;
   d) an interaction identifier, capable of identifying at least one interaction between said at least one host agent and said pathogen agent in a plurality of grids representative of said host;
   e) a simulator, capable of simulating a temporal course of said modeling using said biological event identifier, said agent identifier, said action identifier and said interaction identifier, wherein said simulating is accomplished using an agent-based computational model; and
   f) a displayer, capable of displaying results of said simulating by graphically transforming the results into displays that indicate the predicted outcome of the host-pathogen interaction in a time-phased display; and
   g) wherein said simulator uses an agent-based simulation system comprising:
      1) bidirectional flow at least of at least one of said at least one pathogen agent between at least two of said plurality of grids; and
      2) at least one feedback loop representative at least of at least one said at least one interaction that applies output of at least one of said plurality of grids of the simulation as input for at least another of said plurality of grids of the simulation until an end is met, the end including at least one of:
         i) the host overcomes the pathogen;
         ii) the pathogen overcomes the host; and
         iii) the host becomes tolerant of the pathogen.

16. The analyzer according to claim 15, further including a dataset collector, capable of collecting datasets of said pathogen.

17. The analyzer according to claim 15, further including a series of linked panels, capable of providing a graphical representation or mathematical representation of said host, wherein said series of linked panels comprise at least one of said at least one agent that is modeled.

18. The analyzer according to claim 15, further including a validator, capable of validating said results.

19. The analyzer according to claim 15, further including an intervention identifier, capable of identifying an intervention having at least one of said action, and using said intervention in simulating said temporal course of said host-pathogen interactions.

* * * * *